United States Patent
Kim et al.

(10) Patent No.: US 9,042,686 B2
(45) Date of Patent: May 26, 2015

(54) OPTICAL WAVEGUIDE PLATFORM WITH HYBRID-INTEGRATED OPTICAL TRANSMISSION DEVICE AND OPTICAL ACTIVE DEVICE AND METHOD OF MANUFACTURING THE SAME

(75) Inventors: Hyun Soo Kim, Daejeon (KR); Jong Sool Jeong, Daejeon (KR); Mi-Ran Park, Daejeon (KR); Byungseok Choi, Daejeon (KR); O-Kyun Kwon, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 211 days.

(21) Appl. No.: 13/487,807

(22) Filed: Jun. 4, 2012

(65) Prior Publication Data
US 2013/0163916 A1 Jun. 27, 2013

(30) Foreign Application Priority Data
Dec. 21, 2011 (KR) .......................... 10-2011-0139138

(51) Int. Cl.
| | |
|---|---|
| G02B 6/12 | (2006.01) |
| G02B 6/26 | (2006.01) |
| G02B 6/42 | (2006.01) |
| G02B 6/10 | (2006.01) |
| G02B 6/43 | (2006.01) |
| G02B 6/122 | (2006.01) |

(52) U.S. Cl.
CPC ................ *G02B 6/43* (2013.01); *G02B 6/1228* (2013.01)

(58) Field of Classification Search
CPC .... G02B 6/1228; G02B 6/12004; G02B 6/42; G02B 6/2852
USPC ........................... 385/14, 30, 43, 52, 129–132
See application file for complete search history.

(56) References Cited

U.S. PATENT DOCUMENTS

| | | | |
|---|---|---|---|
| 6,567,590 B1 | 5/2003 | Okada et al. | |
| 2001/0033718 A1* | 10/2001 | Sasaki et al. | 385/88 |
| 2007/0133923 A1 | 6/2007 | Park et al. | |
| 2008/0089697 A1 | 4/2008 | Shen et al. | |
| 2010/0314027 A1* | 12/2010 | Blauvelt et al. | 156/91 |

FOREIGN PATENT DOCUMENTS

KR 10-2005-0049173 A 5/2005

OTHER PUBLICATIONS

Y. Nakasuga et al., "Multi-chip Hybrid Integration on PLC Platform using Passive Alignment Technique", Proceeding of 46th Electronic Components and Technology Conference, May 28-31, 1996, pp. 20-25.

* cited by examiner

Primary Examiner — Kaveh Kianni
Assistant Examiner — Hung Lam
(74) Attorney, Agent, or Firm — Rabin & Berdo, P.C.

(57) ABSTRACT

Disclosed are an optical waveguide platform with integrated active transmission device and monitoring photodiode. The optical waveguide platform with hybrid integrated optical transmission device and optical active device includes an optical waveguide region formed by stacking a lower cladding layer, a core layer and an upper cladding layer on a substrate; a trench region formed by etching a portion of the optical waveguide region; and a spot expanding region formed on the core layer in the optical waveguide region, in which the optical transmission device is mounted in the trench region and the optical active device is flip-chip bonded to the spot expanding region. The monitoring photodiode is flip-chip bonded to the spot expanding region of the core layer of the optical waveguide, thereby monitoring output light including an optical coupling loss that occurs during flip-chip bonding.

7 Claims, 3 Drawing Sheets

OPTICAL WAVEGUIDE PLATFORM WITH HYBRID-INTEGRATED OPTICAL TRANSMISSION DEVICE AND OPTICAL ACTIVE DEVICE AND METHOD OF MANUFACTURING THE SAME

CROSS-REFERENCE TO RELATED APPLICATIONS

This application is based on and claims priority from Korean Patent Application No. 10-2011-0139138, filed on Dec. 21, 2011 with the Korean Intellectual Property Office, the present disclosure of which is incorporated herein in its entirety by reference.

TECHNICAL FIELD

The present disclosure relates to an optical waveguide platform with hybrid-integrated optical transmission device and optical active device and a method of manufacturing the same, and more particularly, to an optical waveguide platform with hybrid-integrated optical transmission device and optical active device that monitors output light of an optical transmission device by flip-chip bonding an optical active device to an upper cladding layer of a planar lightwave circuit (PLC) whose spot size is increased by reducing a line width of a core layer and a method of manufacturing the same.

BACKGROUND

In recent years, with the appearance of high-speed Internet and various multimedia services, a wavelength division multiplexing (WDM) optical communication system has been actively studied in order to provide a massive amount of information.

In the WDM optical communication system, a technology that integrates several optical waveguides corresponding to respective channels in parallel to be implemented at a low cost is required so as to process optical signals of the channels having different wavelengths at a receiver and a transmitter.

In order to reduce costs, it is important to integrate optical active devices such as an optical transmission device, a photodiode and an optical amplifier and optical waveguide devices such as an arrayed waveguide grating (AWG) and an array type variable optical attenuator (VOA). Such optical integration technologies are classified into a monolithic integration technology that implements and integrates an optical active device and an optical waveguide as an optical semiconductor formed of a single material and a planar lightwave circuit hybrid integration technology that integrates an optical active device on a different type of planar lightwave circuit (PLC) platform using flip-chip bonding.

The monolithic integration technology has many limitations in implementing a low-cost optical integrated device due to problems in optimization, reproducibility and yield of each optical device.

Meanwhile, the planar lightwave circuit hybrid integration technology can be implemented with high yield at a low cost since the optical active device and the optical waveguide device each of which is optimized are hybrid-integrated.

However, in the planar lightwave circuit hybrid integration technology, since the optical active device and the optical waveguide device are hybrid-integrated by a flip-chip bonding method, a coupling loss between the optical waveguide device and the optical active device occurs and particularly, there is a high probability of difference in optical loss among channels when an array of optical transmission devices and an array of optical waveguides are hybrid-integrated. Therefore, in order to uniformly maintain the intensity of output light of respective channels in a multi-channel device, a method of monitoring light intensity on an optical waveguide of a planar lightwave circuit is required instead of a method of monitoring light generated from an optical transmission device at a rear end of the optical transmission device.

In the case of a singular planar optical waveguide device such as an AWG and an array type variable optical attenuator, not a planar lightwave circuit device in which an optical active device is hybrid-integrated, intensity of optical signals transmitted to respective channels generally varies for each optical waveguide channel due to an optical coupling loss between channel waveguides and optical fibers, an amplification characteristic for each optical wavelength and a difference in optical transmission paths.

Therefore, in order to exactly transmit signals of multi-channels, a means of readjusting optical signals of channels having different intensity to have uniform intensity is required. In order to readjust the intensity of the optical signal for each of the channels, first, it is required to exactly measure the intensity of the optical signal of each of the optical waveguide.

FIG. 1 is a plan view and a cross-sectional view of an optical waveguide platform with hybrid-integrated optical transmission device and monitoring photodiode in the related art.

Describing a method of manufacturing an optical waveguide platform in the related art, as shown in FIG. 1B, a lower cladding layer 101 and a core layer 102 of an optical waveguide are deposited on a substrate 100. In this case, the substrate 100 may be a silicon substrate or a quartz substrate.

Next, a waveguide pattern is formed on the core layer 102 using photolithography and a dry etching method. An upper cladding layer 103 is deposited on the etched core layer 102 to form a PLC optical waveguide 20. In this case, the lower cladding layer 101, the core layer 102 and the upper cladding layer 103 of the PLC optical waveguide 20 may be formed of silica or a polymer.

In a PLC having the optical waveguide 20, a trench is formed using the photolithography and dry etching method to form a terrace 104 to which an optical transmission device 30 is to be flip-chip bonded, and a terrace 105 to which a monitoring photodiode 40 is flip-chip bonded. In this case, depths of the terraces 104 and 105 are determined so that the height of the terrace 104 is set for the optical transmission device 30 to be mounted and a core layer 111 of the optical transmission device to have the same height and the height of the terrace 105 is set for a monitoring photodiode 40 to be mounted and a core layer 121 to have the same height, and then the terraces 104 and 105 are etched at the determined depths.

As shown in FIG. 1B, an upper cladding layer 110 of the optical transmission device 30 and an upper cladding layer 120 of the monitoring photodiode 40, which are optimized, have different thicknesses and the core layer 111 of the optical transmission device and the core layer 121 of the monitoring photodiode, which are optimized, have different thicknesses.

Since the etching depth of the terrace 104 of the optical transmission device 30 and the etching depth of the terrace 105 of the monitoring photodiode 40 are different from each other as described above, a process of manufacturing an optical waveguide platform becomes complicated.

When the etching depth of the terrace 104 of the optical transmission device 30 and the etching depth of the terrace 105 of the monitoring photodiode 40 are not set differently, thicknesses of a metal line 130, a solder 131 and a flip-chip bonding pad 132 need to be differently set in accordance with the optical transmission device 30 and the monitoring photodiode 40.

The metal line 130 is formed of Cr/Ni/Au, NiCr/Ni/Au, Ti/Ni/Au, Ni/Au and Ti/Pt/Au, and the solder 131 is formed of metal or a metal compound having a low melting point, such as AuSn and In.

The flip-chip bonding pad 132 is formed of Cr/Ni/Au, NiCr/Ni/Au, Ti/Ni/Au, Ni/Au and Ti/Pt/Au.

Meanwhile, as shown in FIG. 1A, when the optical transmission device 30 is flip-chip bonded to the optical waveguide platform, and the monitoring photodiode 40 is flip-chip bonded to a rear end of the optical transmission device 30, an optical coupling loss between the optical transmission device 30 and the monitoring photodiode 40 occurs and thus increases as the distance between the two devices increases. Therefore, in order to minimize the optical coupling loss, the distance between the optical transmission device 30 and the monitoring photodiode 40 is typically set very densely to be 50 µm or less, which makes it difficult to dispose the metal line 50 on the PLC platform. Considering Joule's heat and impedance matching, the metal line 50 has a line width of at least 50 µm.

As shown in FIG. 1A, an array of the optical transmission devices 30 may be bonded to the PLC platform by flip-chip bonding once or a single optical transmission device 30 may be bonded to the PLC optical waveguide by flip-chip bonding several times. Both cases have a problem in that the coupling loss between the optical transmission device and the PLC optical waveguide may vary for each channel by misaligning due to horizontal and vertical directions or inclination during a flip-chip bonding process.

SUMMARY

The present disclosure has been made in an effort to provide a method of manufacturing an optical waveguide platform with a hybrid-integrated monitoring photodiode that can monitor the intensity of output light including an optical coupling loss by monitoring the output light of a PLC optical waveguide while positioning the monitoring photodiode at a front end of an optical transmission device on the PLC optical waveguide.

The present disclosure also has been made in an effort to provide an optical waveguide platform with a hybrid-integrated monitoring photodiode that can monitor the intensity of output light including an optical coupling loss that occurs during flip-chip bonding by forming a spot expanding region with a line width of a core layer of a PLC optical waveguide reduced in a tapering manner and flip-chip bonding a photodiode to an upper cladding layer of the spot expanding region.

A first exemplary embodiment of the present disclosure provides an optical waveguide platform with hybrid-integrated optical transmission device and optical active device, including: an optical waveguide region formed by stacking a lower cladding layer, a core layer and an upper cladding layer on a substrate; a trench region formed by etching a portion of the optical waveguide region; and a spot expanding region formed on the core layer in the optical waveguide region, in which the optical transmission device is mounted in the trench region and the optical active device is flip-chip bonded to the spot expanding region.

A second exemplary embodiment of the present disclosure provides a method of manufacturing an optical waveguide platform with a hybrid-integrated optical transmission device and optical active device, including: sequentially depositing a lower cladding layer and a core layer on a substrate; forming a spot expanding region by reducing a line width or a thickness of the core layer in a tapering manner; depositing an upper cladding layer on the core layer; forming a terrace by partially etching the upper cladding layer, the core layer and the lower cladding layer; flip-chip bonding the optical transmission device to the formed terrace; and flip-chip bonding the optical active device on the upper cladding layer of the spot expanding region.

According to exemplary embodiments of the present disclosure, it is possible to monitor output light including an optical coupling loss that occurs during flip-chip bonding by flip-chip bonding the monitoring photodiode to the upper cladding layer of a PLC with a spot size increased by reducing the line width of the core layer of the optical waveguide.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1A:
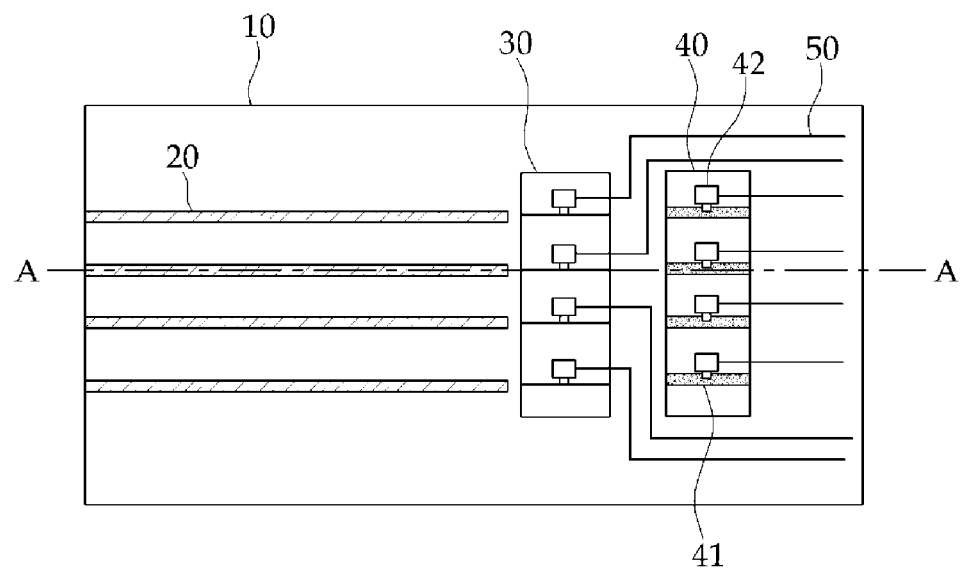
FIGS. 1A and 1B are a plan view and a cross-sectional view of an optical waveguide platform with hybrid-integrated optical transmission device and monitoring photodiode in the related art.
Figure 1B:
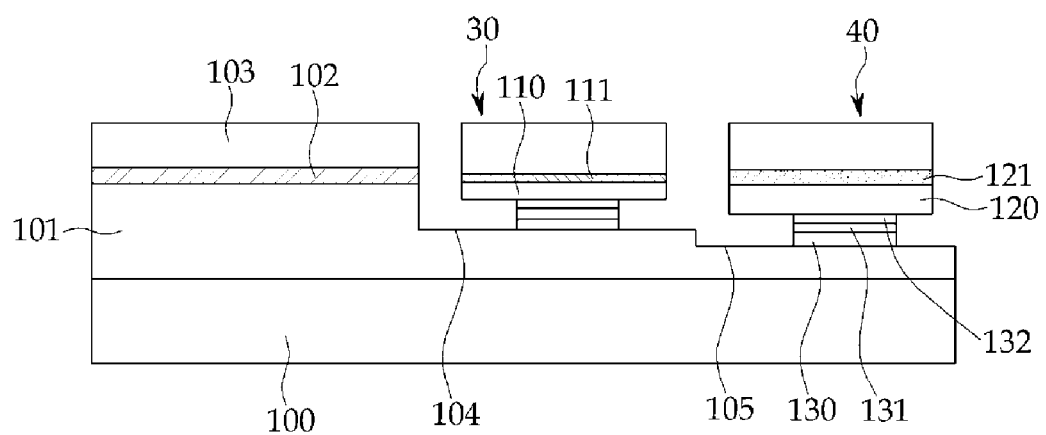

In the following detailed description, reference is made to the accompanying drawing, which form a part hereof. The illustrative embodiments described in the detailed description, drawing, and claims are not meant to be limiting. Other embodiments may be utilized, and other changes may be made, without departing from the spirit or scope of the subject matter presented here.

Hereinafter, exemplary embodiments of the present disclosure will be described in detail with reference to the accompanying drawings. The configurations of the present disclosure and the resulting operational effects will be apparently appreciated through the detailed description described as below. Prior to the detailed description of the present disclosure, like reference numerals refer to like elements as possible even though like elements are shown in different drawings and it is noted that a detailed description of the known configurations will be omitted when it is judged that the known configurations may obscure the spirit of the present disclosure.

Figure 2A:
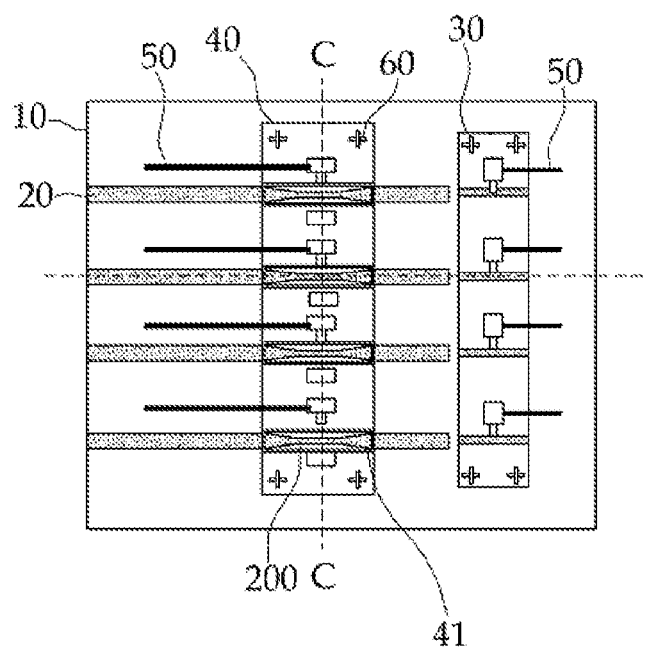
FIG. 2A is a plan view of an optical waveguide platform with hybrid-integrated optical transmission device and monitoring photodiode according to an exemplary embodiment of the present disclosure.
Figure 2B:
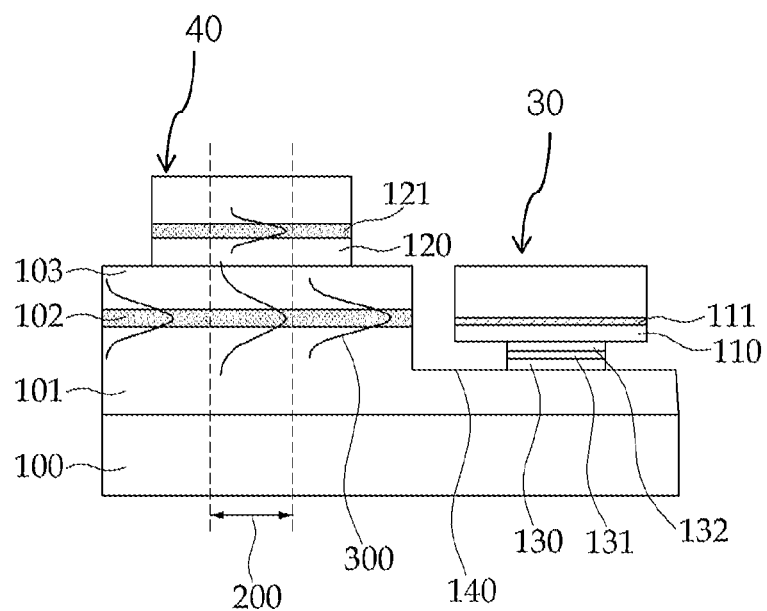
FIG. 2B is a cross-sectional view taken along line B-B' of FIG. 2A.
Figure 2C:
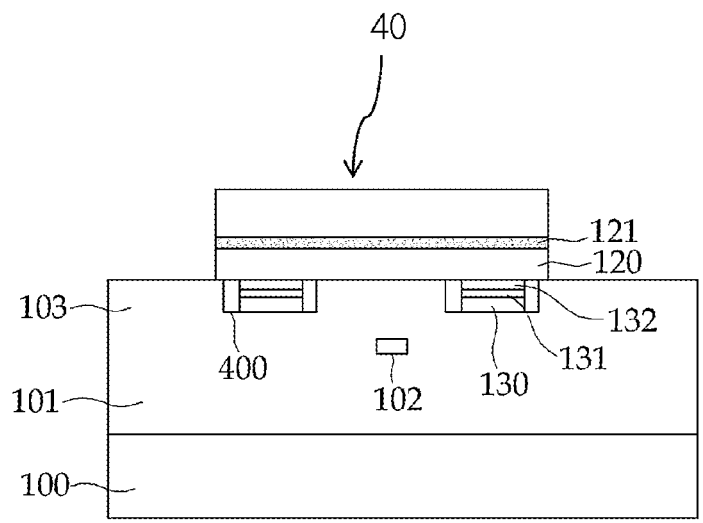
FIG. 2C is a cross-sectional view taken along line C-C' of FIG. 2A.

FIG. 2A is a plan view of an optical waveguide platform with hybrid-integrated optical transmission device and monitoring photodiode according to an exemplary embodiment of the present disclosure, FIG. 2B is a cross-sectional view taken along line B-B' of FIG. 2A, and FIG. 2C is a cross-sectional view taken along line C-C' of FIG. 2A.

Referring to FIG. 2B, in order to manufacture an optical waveguide platform with hybrid-integrated optical transmission device and monitoring photodiode according to the exemplary embodiment of the present disclosure, first, a lower cladding layer 101 and a core layer 102 of an optical waveguide are deposited on a substrate 100.

Next, a waveguide pattern is formed on the core layer 102 using photolithography and a dry etching method. In this case, a spot expanding region 200 having the line width reduced by tapering a line width of the core layer 102 is formed. An upper cladding layer 103 is deposited on the etched silica core layer 102 to form a PLC optical waveguide 20.

In an exemplary embodiment of the present disclosure, the spot expanding region is configured by reducing the line width of the core layer 102 in a tapering manner, but the spot expanding region may also be configured by reducing a thickness of the core layer 102 in a tapering manner.

A lower cladding layer 101, the core layer 102 and the upper cladding layer 103 of the PLC optical waveguide 20 may be formed of silica or a polymer.

A trench region is formed in the PLC having the optical waveguide 20 by using a photolithography and dry etching process to thereby form a terrace 140 to which the optical transmission device 30 is flip-chip bonded. In this case, the etching depth of the terrace 140 is determined such that the optical transmission device 30 to be mounted and a PLC optical waveguide core layer 102 have the same height.

As shown in FIG. 2B, light in the optical waveguide other than the PLC spot expanding region 200 is completely restricted inside the PLC upper cladding layer 103, but a spot size is gradually increased in the PLC spot expanding region 200. Light is evanescently coupled to a monitoring photodiode 40 that is bonded to the upper cladding layer 103 of the spot expanding region 200 by a flip chip bonding method.

Refractive indexes of silica and a polymer used for the lower cladding layer, the core layer and the upper cladding layer of the PLC optical waveguide 20 are 1.45 to 1.7 or less, while a refractive index of InP that is a compound semiconductor used for an optical active device is about 3.167, which is much higher than the refractive indexes. Therefore, light passing through the PLC upper cladding layer 103 is coupled to an absorption layer 121 of the monitoring photodiode 40.

FIG. 2C is a cross-sectional view illustrating when the PLC optical waveguide 20 and the flip-chip bonded monitoring photodiode 40 are flip-chip bonded. As shown in FIG. 2C, the upper cladding layer 103 of the PLC optical waveguide 20 is etched to form a trench 400, thus forming a mounting region of the monitoring photodiode 40. The monitoring photodiode 40 is flip-chip bonded to the mounting region by using an alignment mark.

Therefore, an optical output including an optical coupling loss of the optical transmission device 30 and the PLC optical waveguide 20 may be measured and controlled by the monitoring photodiode 40 mounted according to the exemplary embodiment of the present disclosure.

In the exemplary embodiment of the present disclosure, the optical waveguide platform in which the optical transmission device 30 and the monitoring photodiode 40 are integrated is described, but even in the case of a singular planar optical waveguide device such as an AWG and an array type variable optical attenuator without an optical transmission device, a monitoring photodiode may be flip-chip bonded to a PLC optical waveguide for each channel to detect light intensity.

In the exemplary embodiment of the present disclosure, the monitoring photodiode is flip-chip bonded to the upper cladding layer of the PLC platform, but various optical devices such as an optical amplifier, an optical attenuator and an optical transmission device in addition to the monitoring photodiode may be flip-chip bonded thereto.

Figure 3:
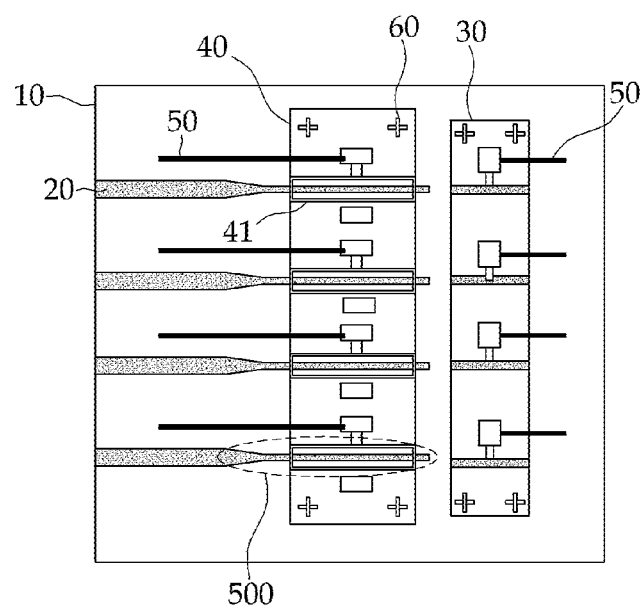
FIG. 3 is a plan view of an optical waveguide platform in which an optical transmission device, a monitoring photodiode and a spot size converter (SSC) are hybrid-integrated according to an exemplary embodiment of the present disclosure.

FIG. 3 is a plan view of an optical waveguide platform in which an optical transmission device, a monitoring photodiode and a spot size converter (SSC) are hybrid-integrated according to the exemplary embodiment of the present disclosure.

In order to increase optical coupling between the PLC waveguide 20 and the flip-chip bonded optical transmission device 30, and a misalignment tolerance which occurs when the optical transmission device 30 is flip-chip bonded to the optical waveguide platform 10, an SSC 500 is integrated.

In this case, the SSC 500 reduces a line width of the PLC waveguide 20 in a tapering manner to increase a spot size. Therefore, when the monitoring photodiode 40 is flip-chip bonded to the upper cladding layer of the optical waveguide platform 10 in a region of the SSC 500, the spot is partially absorbed, which makes it possible to detect light intensity. In this case, as the width of the optical waveguide is reduced, the spot size increases. Therefore, the light intensity absorbed in the monitoring photodiode 40 is increased.

In the present disclosure, the optical waveguide platform with the integrated optical transmission device and monitoring photodiode is described, but even in the case of a singular planar optical waveguide device such as an AWG and an array type variable optical attenuator without an optical transmission device, a monitoring photodiode may be flip-chip bonded to the PLC optical waveguide for each channel to detect light intensity.

In the present disclosure, the monitoring photodiode is flip-chip bonded to the upper cladding layer of the PLC platform, but various optical devices such as an optical amplifier, an optical attenuator and an optical transmission device in addition to the monitoring photodiode may be flip-chip bonded thereto.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A method of manufacturing an optical waveguide platform with a hybrid-integrated optical transmission device and optical active device, comprising:
    sequentially depositing a lower cladding layer and a core layer of an optical waveguide on a substrate;
    forming a spot expanding region by reducing a line width or a thickness of the core layer in a tapering manner;
    depositing an upper cladding layer of the optical waveguide on the core layer;
    forming a terrace by partially etching the upper cladding layer, the core layer and the lower cladding layer of the optical waveguide;
    flip-chip bonding the optical transmission device to the formed terrace; and
    flip-chip bonding the optical active device on the upper cladding layer of the optical waveguide adjacent the spot expanding region and at a front end of the optical transmission device on the optical waveguide.

2. The method of claim 1, wherein in the flip-chip bonding of the optical active device, the optical active device is positioned by using an alignment mark formed on the optical active device and an alignment mark formed on the upper cladding layer of the optical waveguide before flip-chip bonding the optical active device.

3. The method of claim 1, wherein the terrace has a height so that the optical transmission device to be mounted and the core layer have the same height.

4. The method of claim 1, wherein the lower cladding layer, the core layer and the upper cladding layer of the optical waveguide are formed of silica or a polymer.

5. The method of claim 1, wherein the spot expanding region is a spot size converter.

6. The method of claim 1, wherein the optical active device is a photodiode, an optical modulator, an optical amplifier, an optical attenuator and an optical transmission device.

7. A method of manufacturing an optical waveguide platform with a hybrid-integrated optical transmission device and optical active device, comprising:

sequentially depositing a lower cladding layer and a core layer of an optical waveguide on a substrate;

forming a spot expanding region by reducing a line width or a thickness of the core layer in a tapering manner;

depositing an upper cladding layer of the optical waveguide on the core layer;

forming a terrace by partially etching the upper cladding layer, the core layer and the lower cladding layer of the optical waveguide;

flip-chip bonding the optical transmission device to the formed terrace; and flip-chip bonding the optical active device on the upper cladding layer of the optical waveguide adjacent the spot expanding region, such that an upper cladding layer of the optical active device opposes and contacts the upper cladding layer of the optical waveguide.

* * * * *